(12) United States Patent
Coffland (10) Patent No.: US 9,119,276 B2
(45) Date of Patent: Aug. 25, 2015

(54) ELECTROSTATIC CHARGE DISSIPATION SYSTEM

(71) Applicant: The Boeing Company, Chicago, IL (US)

(72) Inventor: Donald W. Coffland, Seattle, WA (US)

(73) Assignee: The Boeing Company, Chicago, IL (US)

( * ) Notice: Subject to any disclaimer, the term of this patent is extended or adjusted under 35 U.S.C. 154(b) by 176 days.

(21) Appl. No.: 13/941,891

(22) Filed: Jul. 15, 2013

(65) Prior Publication Data

US 2015/0016009 A1     Jan. 15, 2015

(51) Int. Cl.
    *H05F 3/00*        (2006.01)
    *H05F 3/02*        (2006.01)
    *A61N 1/14*        (2006.01)
    *H05K 9/00*        (2006.01)

(52) U.S. Cl.
    CPC .. *H05F 3/02* (2013.01); *A61N 1/14* (2013.01); *H05F 3/00* (2013.01); *H05K 9/0067* (2013.01)

(58) Field of Classification Search
    CPC ........................................................ H05F 3/00
    USPC ........................................................ 361/220
    See application file for complete search history.

(56) References Cited

U.S. PATENT DOCUMENTS

| | | | |
|---|---|---|---|
| 3,745,412 A | 7/1973 | Ruff | |
| 4,104,695 A * | 8/1978 | Hollis et al. | 361/220 |
| 4,698,724 A * | 10/1987 | Burvee | 361/220 |
| 4,800,374 A | 1/1989 | Jacobson | |
| 5,222,013 A | 6/1993 | Schwalm | |
| 5,768,086 A | 6/1998 | Abe | |
| 6,778,376 B2 | 8/2004 | Soper | |
| 2002/0080549 A1 | 6/2002 | Wertsberger | |
| 2008/0192403 A1 | 8/2008 | Chen | |
| 2009/0116164 A1 | 5/2009 | Chen et al. | |

OTHER PUBLICATIONS

Extended European Search Report, EP 14 17 6888 (2014).

* cited by examiner

*Primary Examiner* — Scott Bauer
(74) *Attorney, Agent, or Firm* — Walters & Wasylyna LLC (57) ABSTRACT

An electrostatic charge dissipation system including an electrostatic discharge assembly configured to connect to a conductive article, the electrostatic discharge assembly including a conductor, an insulator positioned between the conductor and the conductive article, and an indicator electrically connected to the conductor and the conductive article, the indicator being configured to indicate a discharge of an electrostatic charge.

20 Claims, 7 Drawing Sheets

ELECTROSTATIC CHARGE DISSIPATION SYSTEM

FIELD

The present disclosure is generally related to electrostatic discharge and, more particularly, to a system and method for passive dissipation of an electrostatic charge.

BACKGROUND

In certain conditions, a substantial amount of electrostatic charge may develop on a human body. The rapid discharge of an electrostatic charge, for example by touching a conductive object, may result in an uncomfortable and sudden static electric shock. Dry air conditions may increase the accumulation of electrostatic charge, such as those conditions found in climate-controlled areas.

Static discharge devices, such as grounding straps worn on a user's wrist or grounding mats positioned on the floor, may reduce or eliminate electrostatic charge buildup. However, such devices are not always practical. For example, grounding straps may be inconvenient in settings where a person must move around considerably and grounding mats may obstruct movement of rolling work stands.

Accordingly, those skilled in the art continue with research and development efforts in the field of electrostatic charge dissipation.

SUMMARY

In one embodiment, the disclosed electrostatic charge dissipation system may include an electrostatic discharge assembly configured to connect to a conductive article, the electrostatic discharge assembly including a conductor, an insulator positioned between the conductor and the conductive article, and an indicator electrically connected to the conductor and the conductive article, the indicator being configured to visually indicate a discharge of an electrostatic charge from a human body.

In another embodiment, the disclosed electrostatic charge dissipation system may include a conductive article and an electrostatic discharge assembly connected to the conductive article, the electrostatic discharge assembly including a conductor including an electrically conductive material, an insulator including an electrically insulative material, the insulator being positioned between the conductor and the conductive article, an indicator electrically connected between the conductor and the conductive article, wherein an electrostatic charge brought into close approximation of the conductor will cause the electrostatic charge to be discharged through the indicator, the indicator being configured to visually indicate the discharge of the electrostatic charge.

In yet another embodiment, disclosed is a method for dissipation of an electrostatic charge, the method may include the steps of: (1) providing a conductive article, (2) providing an electrostatic discharge assembly including a conductor, an insulator positioned between the conductor and the conductive article, and an indicator electrically connected to the conductor and the conductive article, (3) installing the electrostatic discharge assembly to the conductive article, (4) approximating a human body having a developed electrostatic charge to the electrostatic discharge assembly, (5) discharging the electrostatic charge, and (6) confirming discharge of the electrostatic charge by visual observation of the indicator.

Other embodiments of the disclosed system and method for dissipation of an electrostatic charge will become apparent from the following detailed description, the accompanying drawings and the appended claims.

DETAILED DESCRIPTION

The following detailed description refers to the accompanying drawings, which illustrate specific embodiments of the disclosure. Other embodiments having different structures and operations do not depart from the scope of the present disclosure. Like reference numerals may refer to the same element or component in the different drawings.

Figure 1:
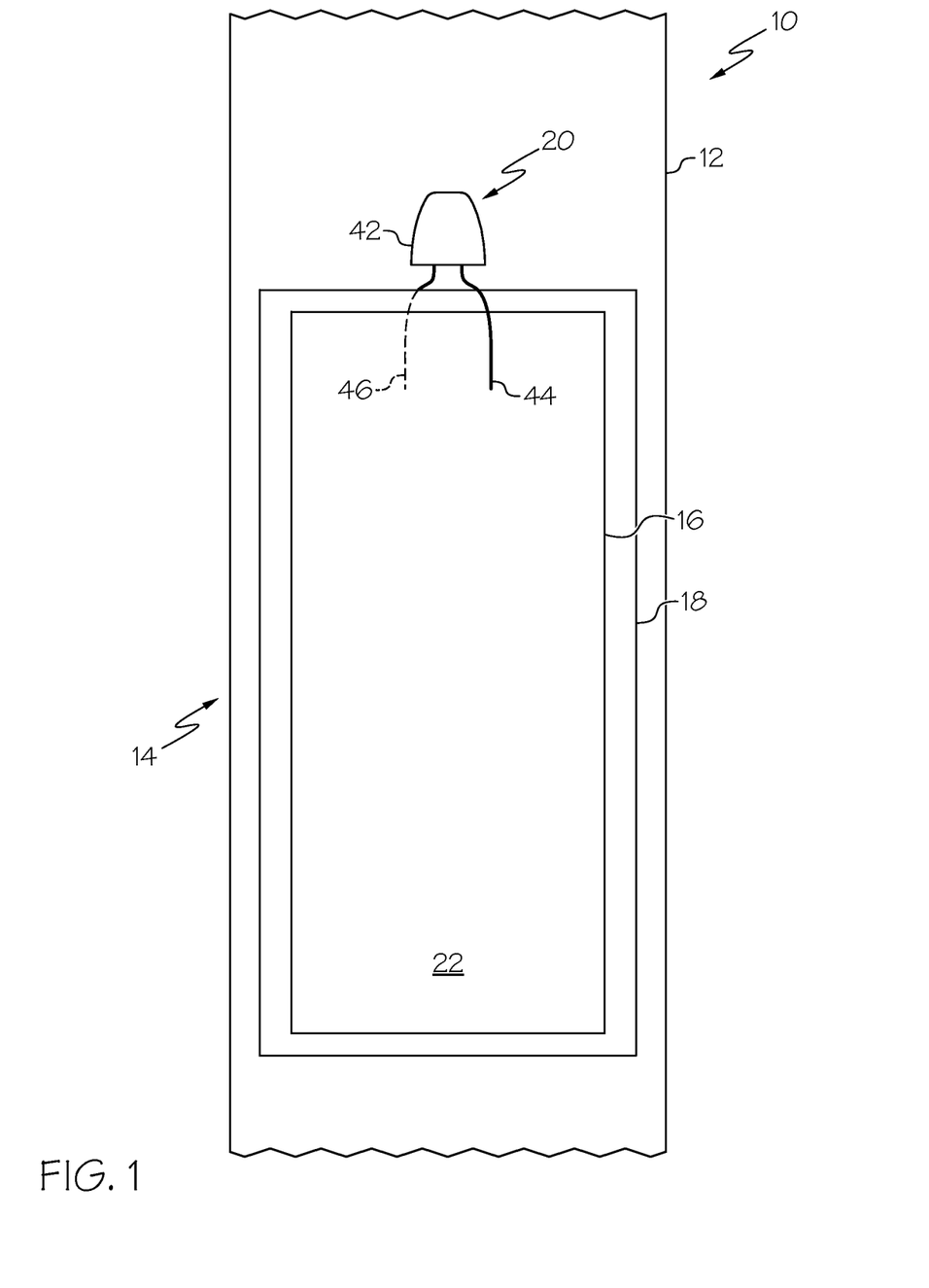
FIG. 1 is a top plan view of one embodiment of the disclosed electrostatic charge dissipation system.

Referring to FIG. 1, one embodiment of the disclosed electrostatic charge dissipation system, generally designated 10, may include a conductive article 12 and an electrostatic discharge assembly 14 connected to a surface of the conductive article 12. The electrostatic discharge assembly 14 may include a conductor 16, an insulator 18, and an indicator 20.

Figure 2:
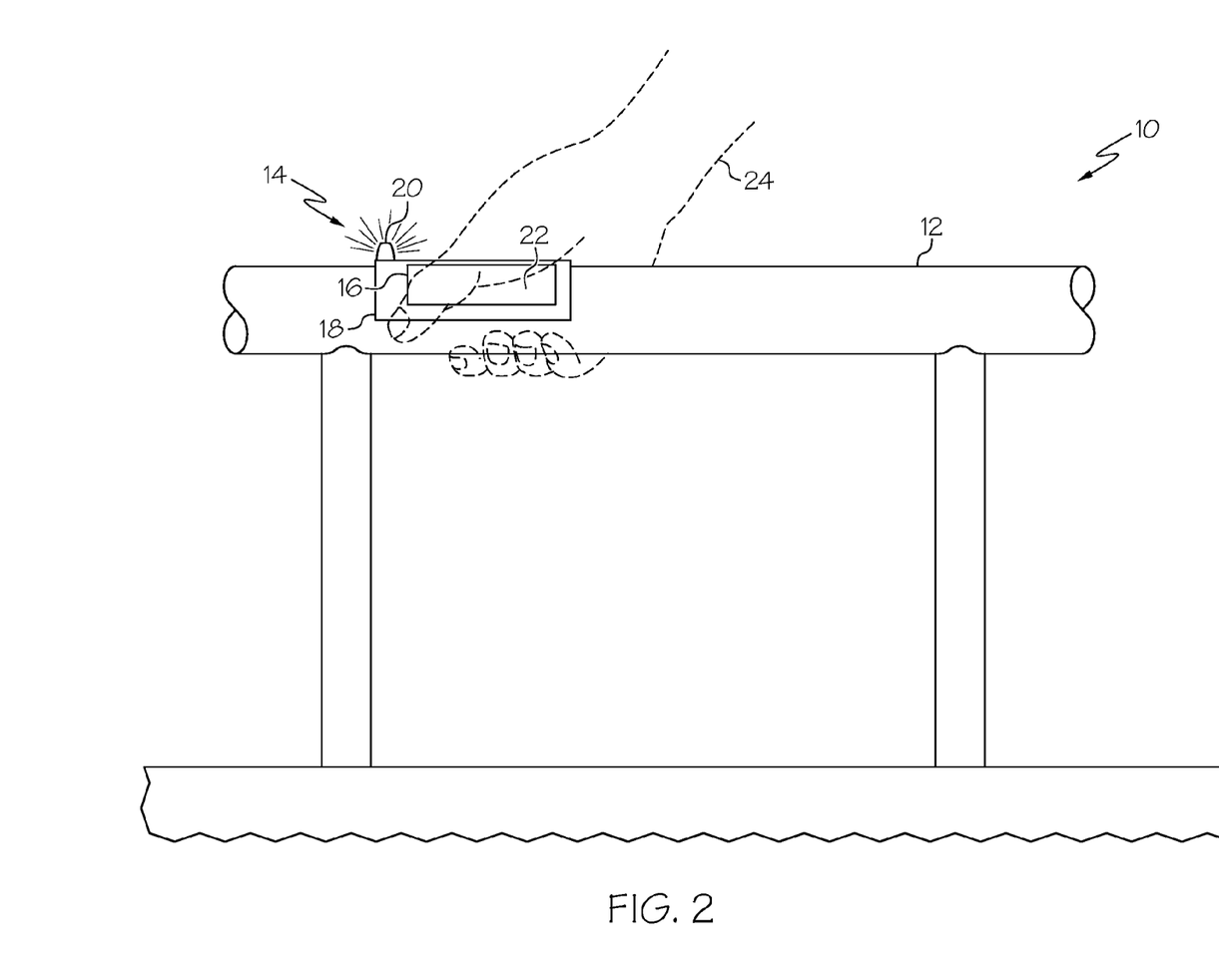
FIG. 2 is an environmental view of the disclosed electrostatic charge dissipation system.

The conductor 16 may include a conductive contact surface 22 configured to be contacted by at least a portion of a human body 24 (e.g., a human hand), as illustrated in FIG. 2. The insulator 18 may be disposed between the conductor 16 and the conductive article 12 in order to electrically isolate the conductor 16 and the conductive article 12 from one another.

The indicator 20 may be configured to provide a resistance to the electrostatic potential of an electrostatic charge that may develop on a person. The indicator 20 may limit the magnitude and extend the duration of a current flow from the discharge of the electrostatic charge, thus any hurtful or uncomfortable sensation (e.g., shock) received by the charged person may be lessened or eliminated. The indicator 20 may provide a visual indication of the discharge of the electrostatic charge.

Referring to FIG. 2, the electrostatic discharge assembly 14 may be connected, installed, or otherwise attached (e.g., integral) to at least one surface of the conductive article 12. The conductive article 12 may be any metallic member or object (e.g., a grounded metallic object). The electrostatic discharge assembly 14 may be connected at any position upon the surface of the conductive article 12. For example, the electrostatic discharge assembly 14 may be positioned such that it is readily available for use by a person having a need to discharge an electrostatic charge.

An electric discharge or current may travel from the conductive surface 22 of the conductor 16 through the indicator 20 and into the conductive article 12. Thus, by touching the conductor 16, an electrostatic charge on a human body may be dissipated by the electrostatic discharge assembly 14 through the hand 24 or fingers, which may prevent the person from getting an electric shock due to static electricity when initially contacting the conductive article 12.

In an example implementation, the conductive article 12 may be a metallic handrail and the electrostatic discharge assembly 14 may be connected to a surface of the handrail in a position that is naturally touched or gripped by a human hand as a person approaches the handrail, such as being positioned about an upper surface and/or side surface of the handrail. In another example implementation, the conductive article 12 may be a metallic workbench and the electrostatic discharge assembly 14 may be connected to a surface of the workbench in a position that is naturally touched or gripped by the human hand as a person approaches the workbench, such as being positioned about an edge of an upper surface and/or side surface of the workbench. In yet another example implementation, the conductive article 12 may be a metallic handle and the electrostatic discharge assembly 14 may be connected to a surface of the handle in a position that is naturally touched or gripped by the human hand as a person approaches the handle, such as being positioned about a side edge and/or a front surface of the handle.

Figure 3:
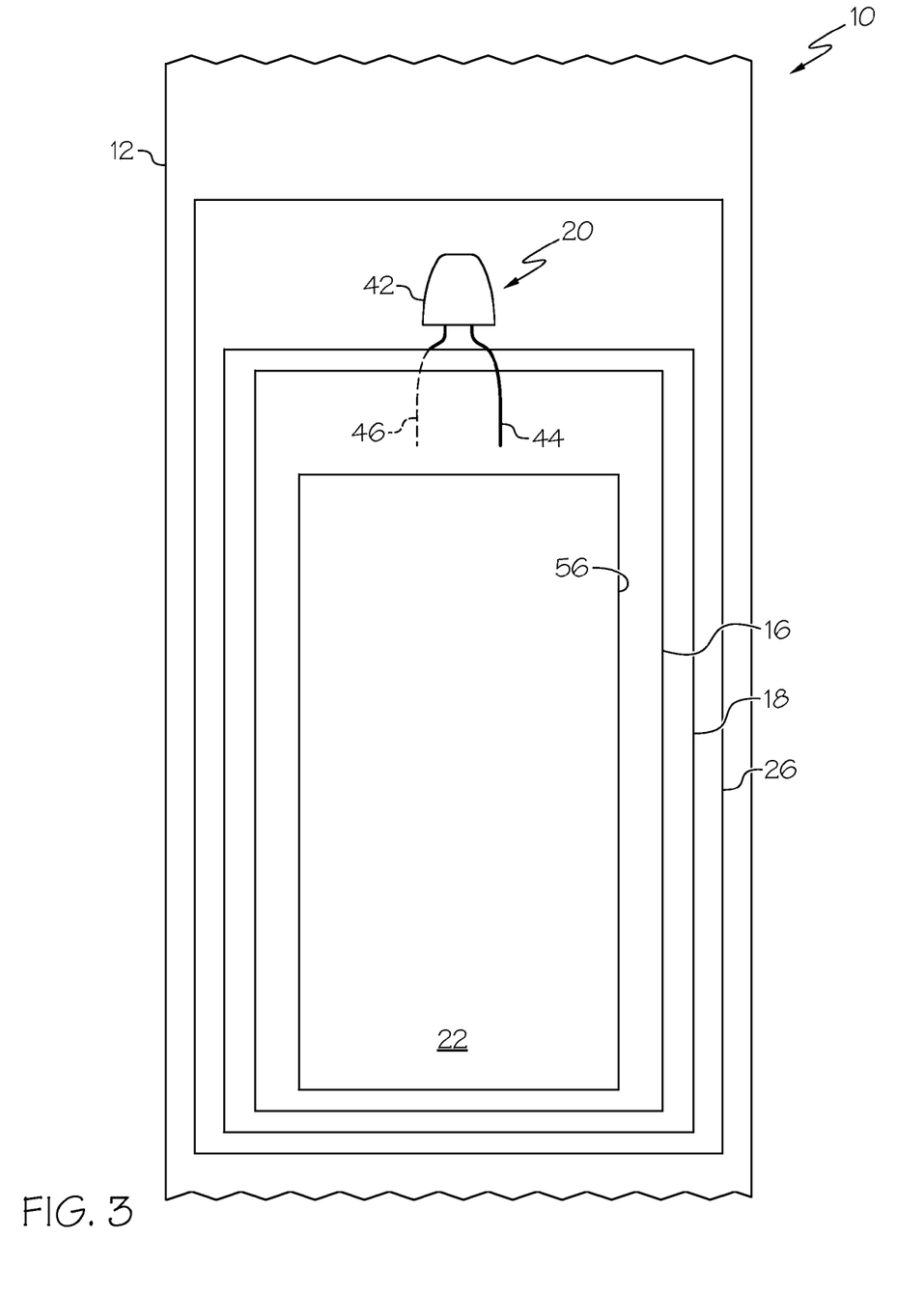
FIG. 3 is a top plan view of another embodiment of the disclosed electrostatic charge dissipation system.

Referring to FIG. 3, optionally, the electrostatic discharge assembly 14 may include a protector 26. The protector 26 may be positioned overtop of the insulator 18, the conductor 16, and the indicator 20. The protector 26 may be configured to cover and protect the insulator 18, the conductor 16, and the indicator 20 and/or connect the electrostatic discharge assembly 14 to the conductive article 12. The protector 26 may include a cutout formed through an interior area defining a window 56. The window 56 may expose a portion of the conductor 16 and define the exposed conductive surface 22.

Figure 4:
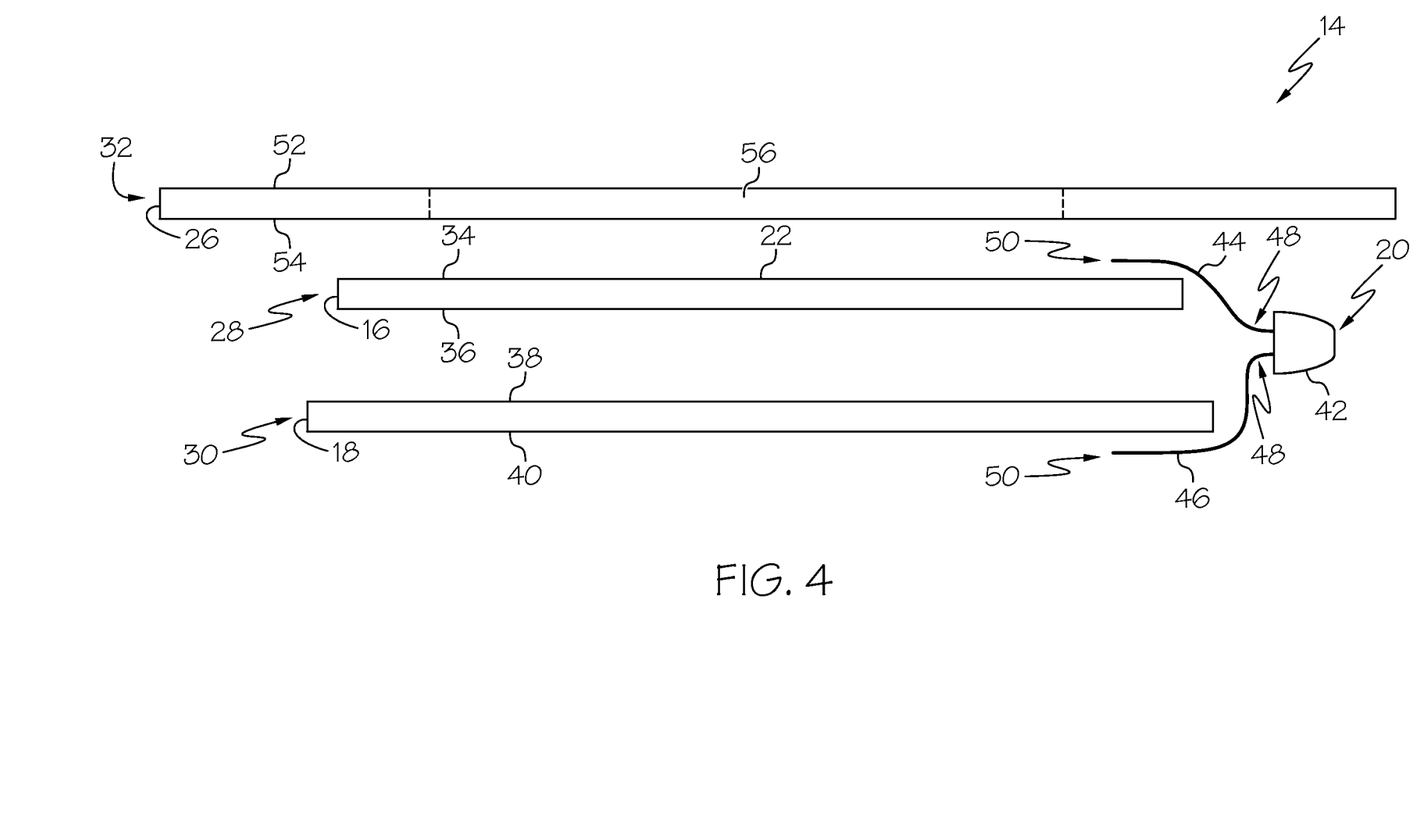
FIG. 4 is an exploded side elevational view of the disclosed electrostatic charge dissipation assembly.

Referring to FIG. 4, the conductor 16 may be formed of any suitable conductive material, such as a metallic material. For example, the conductor 16 may be a conductive (e.g., metallic) substrate defining a conductive layer 28. As a specific non-limiting example, the conductor 16 may be metallic tape, such as aluminum foil tape, copper foil tape, or the like. As another specific non-limiting example, the conductor 16 may a thin strip of metal.

The insulator 18 may be formed of any suitable insulative material. For example, the insulator 18 may be an insulative substrate defining an insulative layer 30. As a specific non-limiting example, the insulator 18 may be electrical tape. As another specific non-limiting example, the insulator 18 may be foam tape. As yet another specific non-limiting example, the insulator 18 may be a thin strip of insulation.

The protector 26 may be formed of any suitable material (e.g., a flexible material) capable of covering the conductor 16, the insulator 18, and the indicator 20 and being connected to the surface of the conductive article 12. For example, the protector 26 may be a protective substrate defining a protective layer 32. The protector 26 may also be formed of an insulative material in order to electrically isolate the perimeter edges of the conductor 16 and the insulator 18 and the indicator 20. As a specific non-limiting example, the protector 26 may be packaging tape. As another specific non-limiting example, the protector 26 may be electrical tape. The protector 26 may be transparent to provide for visual observation of the indicator 20 covered by the protector 26. Alternatively, the protector 26 may include a second cutout defining an access opening (not shown) configured to expose the indicator 20.

The indicator 20 may include an indicator light 42 electrically connected between the conductor 16 and the conductive article 12. The indicator light 42 may be any bulb or lamp capable of being briefly energized by the high voltage and low current produced by the discharge of an electrostatic charge. As a specific non-limiting example, the indicator light 42 may be a static electric bulb (also referred to as a human powered bulb). As another specific non-limiting example, the indicator light 42 may be a neon bulb (e.g., neon pilot bulb).

The indicator 20 may include a first terminal 44 and a second terminal 46. Each terminal 44, 46 may include a first end 48 electrically connected to the indicator light 42 and an opposed (e.g., free) second end 50. The second end 50 of the first terminal 44 may be in electrical contact with the conductor 16 and the second end 50 of the second terminal 46 may be in electrical contact with the conductive article 12 in order to provide a path for the electrostatic charge to travel from the human body 24 (FIG. 2) to the grounded conductive article 12 upon contact with the conductive surface 22 of the conductor 16.

Referring still to FIG. 4, the conductor 16 may include a first major surface 34 and an opposed second major surface 36. At least a portion of the first major surface 34 of the conductor 16 may define the conductive surface 22. The insulator 18 may include a first major surface 38 and an opposed second major surface 40. The protector 26 may include a first major surface 52 and an opposed second major surface 54. The window 56 may define at least a portion of an interior area of the protector 26 and expose an area of the conductor 16, thus exposing at least a portion of the first major surface 34 of the conductor 16 defining the conductive surface 22.

Figure 5:
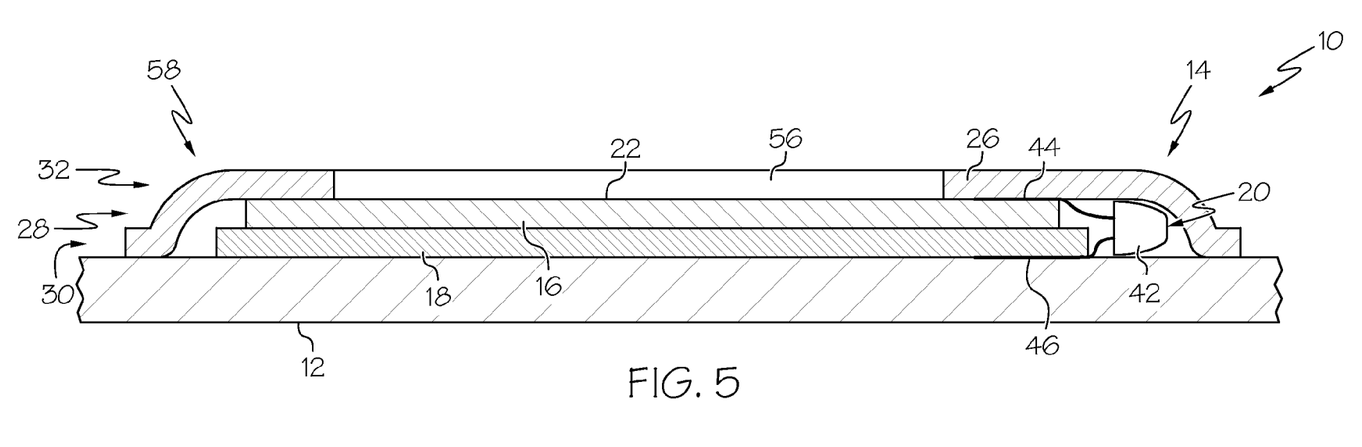
FIG. 5 is a side elevational view, in section, of the disclosed electrostatic charge dissipation system of FIG. 3.

Referring to FIGS. 4 and 5, in an example construction, the conductive layer 28, the insulator layer 30, and the protective layer 32 may each be built up to form a laminated assembly 58. The insulator 18 may be applied to the conductive article 12, for example by connecting the second major surface 40 of the insulator 18 to a surface of the conductive article 12. The conductor 16 may be applied to the insulator 18, for example by connecting the second major surface 36 of the conductor 16 to the first major surface 38 of the insulator 18, such that the insulator 18 is positioned entirely between the conductor 16 and the conductive article 12.

The first terminal 44 may be electrically connected to the conductor 16. For example, the second end 50 of the first terminal 44 may be mechanically secured to the conductor 16, such as by soldering, brazing, or the like. As another example, the second end 50 of the first terminal 44 may be positioned in physical contact with the first major surface 34 of the conductor 16. The optional protector 26 may be applied to the conductor 16, for example by connecting the second major surface 54 of the protector 26 to the first major surface 34 of the conductor 16, such that the first terminal 44 is positioned (e.g., sandwiched) between the protector 26 and the conductor 16, as illustrated in FIG. 5.

The second terminal 46 may be electrically connected to the conductive article 12. For example, the second terminal 46 may be mechanically secured to the insulator, such as by adhesives or the like, such that the second end 50 of the second terminal 46 is at least partially exposed to contact the conductive article 12 upon application of the insulator 18. As another example, the second end 50 of the second terminal 46 may be positioned in physical contact with the surface of the conductive article 12, such that the second terminal 46 is positioned (e.g., sandwiched) between the insulator 18 and the conductive article 12, as illustrated in FIG. 5.

Figure 6:
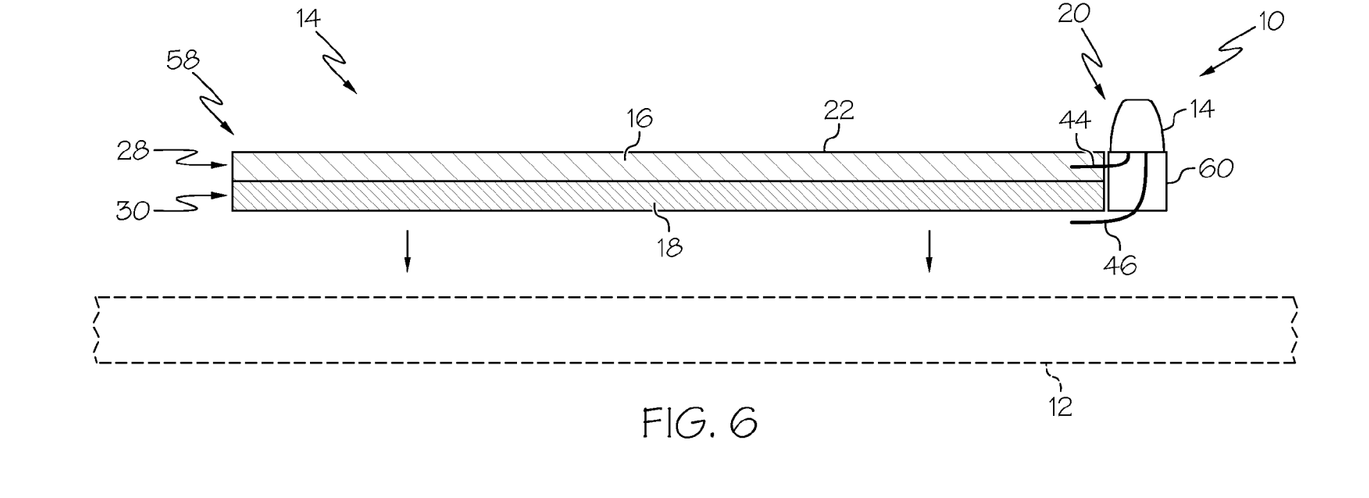
FIG. 6 is a side elevational view of another embodiment of the disclosed electrostatic charge dissipation system.

Referring to FIG. 6, in another example construction of the disclosed system 10, the conductor 16, the insulator 18, the indicator 20, and optionally the protector 26 (not shown in FIG. 6) may be pre-connected or pre-assembled to form the laminated assembly 58, such that the laminated assembly 58 may be connected to the conductive article 12.

The indicator 20 may include a light housing 60. The light housing 60 may be connected to a peripheral edge of the laminated assembly 58. The light housing 60 may house and protect the indicator light 42 and position and protect the terminals 44, 46 for connection to the conductor 16 and the conductive article 12. The light housing 60 may be beneficial for constructions of the electrostatic discharge assembly 14 not including the protector 26, as illustrated in FIG. 6.

Referring back to FIGS. 4 and 5, the conductive layer 28, the insulator layer 30, and the protective layer 32 may each be connected by any suitable technique. For example, the insulator 18 and/or the protector 26 may be connected to the conductive article 12 and the insulator 18, the conductor 16, and the protector 26 may be connected to each other by adhesive bonding. As a specific non-limiting example, an adhesive may be applied between contacting major surfaces (e.g., between the second major surface 40 of the insulator 18 and the surface of the conductive article 12, between the second major surface 36 of the conductor 16 and the first major surface 38 of the insulator 18, etc.). As another specific non-limiting example, adhesive may be pre-applied to the second major surfaces 36, 40, 54 of the conductor 16, insulator 18, and protector 26 (e.g., adhesive tape), such that each layer 28, 30, 32 may be connected to a directly adjacent layer upon contact. As another specific non-limiting example, the conductor 16, the insulator 18, and the indicator 20 may be positioned (e.g., sandwiched) between the protector 26 and the conductive article 12, such that only the second major surface 54 of the protector 26 is connected (e.g., adhesively bonded) to the surface of the conductive article 12.

Those skilled in the art will appreciate that the overall size and shape of the conductor 16, the insulator 18, and the protector 26 may vary depending upon the conductive article 12 or the surface are of the conductive article 12 being covered by the laminated assembly 58. For example, the conductor 16, the insulator 18, and the protector 26 may include a generally rectangular shape, a generally circular shape, or any other geometric shape.

In an example implementation of the described constructions, the surface areas of the conductor 16, the insulator 18, and the protector 26 may be substantially equal. In another example implementation of the described constructions, the surface areas of the conductor 16, the insulator 18, and the protector 26 may be substantially different.

Referring again to FIG. 1, the insulator 18 may have a surface area greater than the surface area of the conductor 16, such that peripheral edges of the insulator 18 extend beyond the peripheral edges of the conductor 16. For example, the surface area of the insulator 18 may be at least 5 percent greater than the surface area of the conductor 16. As another example, the surface area of the insulator 18 may be at least 10 percent greater than the surface area of the conductor 16. As another example, the surface area of the insulator 18 may be at least 20 percent greater than the surface area of the conductor 16. As another example, the surface area of the insulator 18 may be at least 30 percent greater than the surface area of the conductor 16. As yet another example, the surface area of the insulator 18 may be at least 50 percent greater than the surface area of the conductor 16.

Referring again to FIG. 3, the protector 26 may have a surface area greater than the surface area of the conductor 16 and the insulator 18, such that peripheral edges of the protector 26 extend beyond the peripheral edges of the conductor 16 and optionally cover the indicator 20. For example, the surface area of the protector 26 may be at least 10 percent greater than the surface area of the insulator 18. As another example, the surface area of the protector 26 may be at least 20 percent greater than the surface area of the insulator. As another example, the surface area of the protector 26 may be at least 50 percent greater than the surface area of the insulator. As another example, the surface area of the protector 26 may be at least 75 percent greater than the surface area of the insulator.

The window 56 may be suitably sized to expose a substantial area of the first major surface 34 of the conductor 16 defining the conductive contact surface 22. For example, the window 56 may be sized to expose at least 50 percent of the first major surface 34 of the conductor 16. As another example, the window 56 may be sized to expose at least 60 percent of the first major surface 34 of the conductor 16. As another example, the window 56 may be sized to expose at least 75 percent of the first major surface 34 of the conductor 16.

Figure 7:
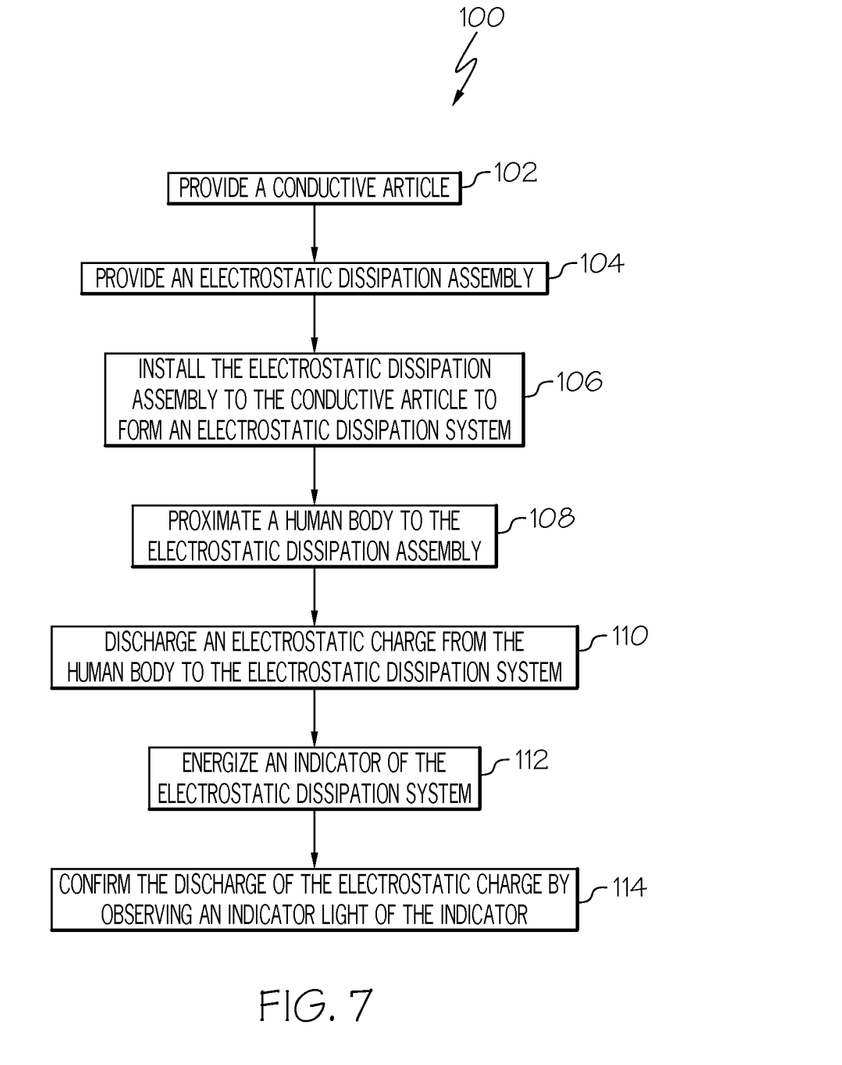
FIG. 7 is a flow diagram of one embodiment of the disclosed method for dissipation of an electrostatic charge.

Referring now to FIG. 7, also disclosed is a method, generally designated 100, for dissipation of an electrostatic charge. As shown at block 102, the method 100 may begin with the step of providing the conductive article 12 (FIG. 2). The conductive article 12 may include any metallic object, particularly a grounded metallic object, such as a handrail, a workbench, or the like, which may deliver an electric shock due to the rapid discharge of static electricity developed on a person's body 24 (FIG. 2) when touched by the person.

As shown at block 104, the electrostatic discharge assembly 14 (FIG. 2) may be provided. As illustrated in FIG. 4, the electrostatic discharge assembly 14 may include the conductor 16 defining the conductive layer 28, the insulator 18 defining the insulative layer 28, the indicator 20, and, optionally, the protector 26 defining the protective layer 32. The conductive layer 28, insulative layer 28, and protective layer 32 may form the laminated assembly 58.

As shown at block 106, the electrostatic discharge assembly 14 may be installed (e.g., connected) to the conductive article 12 to form the electrostatic dissipation system 10. As illustrated in FIG. 5, the electrostatic discharge assembly 14 may be installed such that the first terminal 44 of the indicator 20 is in electrical contact with the conductor 16 and the second terminal 46 is in electrical contact with a surface of the conductive article 12. The first terminal 44 and the second terminal 46 may be electrically isolated by the insulator 18.

As shown at block 108, a portion of the human body 24 (FIG. 2) having a developed electrostatic charge may approximate the electrostatic dissipation system 10. For example, the human hand or finger may closely approach or touch the conductive surface 22 of the conductor 16, as illustrated in FIG. 2.

As shown at block 110, the electrostatic charge may discharge from the human body 24 to the electrostatic dissipation system 10 (e.g., from the human body 24 to the conductive article 12 through the electrostatic discharge assembly 14) (FIG. 2). The static electricity may travel (1) from the human body 24 to the conductor 16 upon contact (or near contact), (2) from the conductor 16 to the indicator 20 (e.g., via the first terminal 44), and (3) through the indicator 20 to the conductive article 12 (e.g., via the second terminal 46).

As shown at block 112, the electrostatic charge may energize the indicator 20 and illuminate the indicator light 42 (FIG. 5). The indicator light 42 may provide sufficient resistance to the electrical potential of the electrostatic charge to dissipate the electrostatic charge.

As shown at block 114, the person may confirm that any electrostatic charge has been completely discharged by visually observing the illumination of the indicator light 42. For example, when indicator light 42 is illuminated, it means that the electrostatic discharge assembly 14 is operating and dissipating the electrostatic charge. When illumination of the indicator light 42 ceases, it means that the electrostatic discharge is complete and the person may touch the conductive article 12 without getting an electric shock due to static electricity on the body.

Accordingly, the disclosed system and method for dissipation of an electrostatic charge may be readily available for the discharge of an electrostatic charge from a person's body without the need for the person to wear a personal antistatic device. Any charge generated by static electricity will exit through the conductor instead of the person's body (e.g., hand or finger). This effectively eliminates the static in the body without feeling pain of a shock due to the discharge (e.g., static electric arc) of electricity leaving the body. Additionally, the indicator provides visual indication that any electrostatic charge has dissipated from the body, thus making it more likely that a person will utilize the disclosed system.

Figure 8:
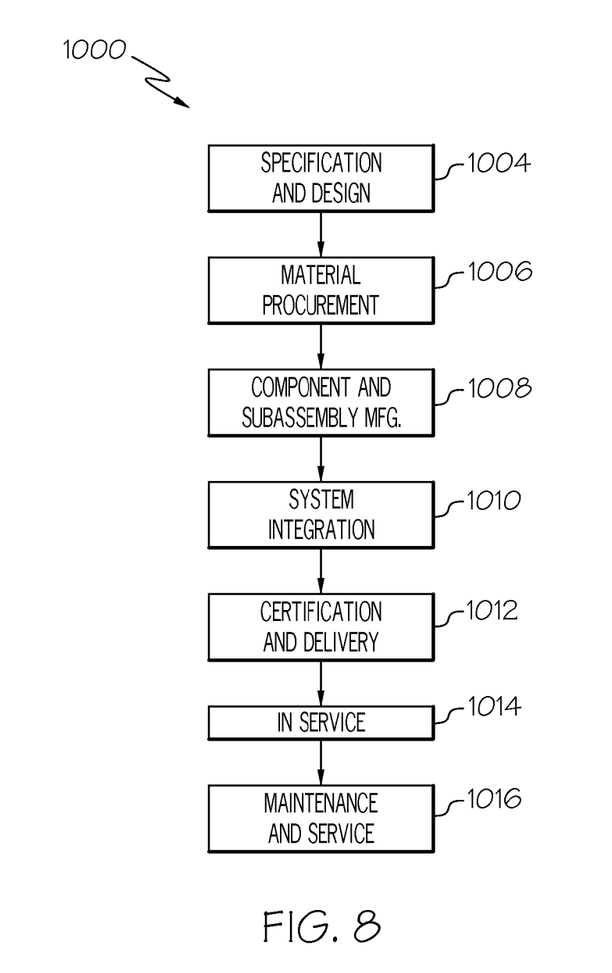
FIG. 8 is a flow diagram of aircraft production and service methodology.
Figure 9:
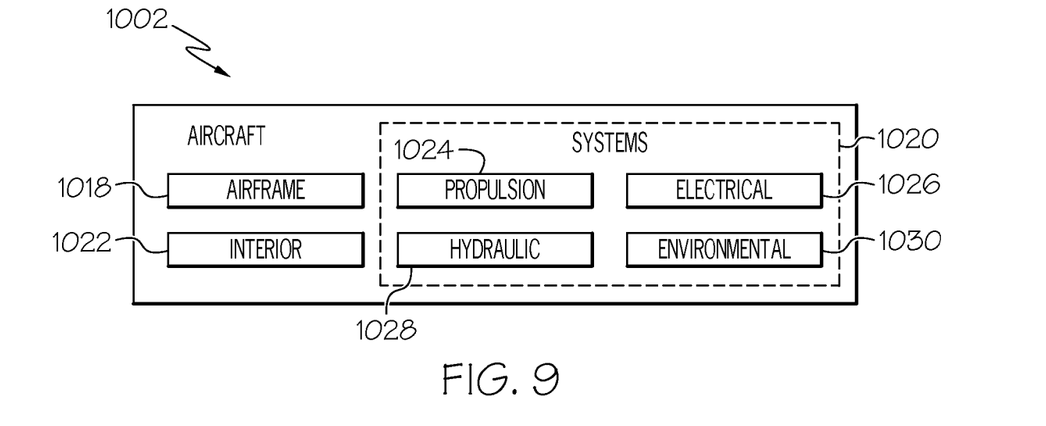
FIG. 9 is a block diagram of an aircraft.

Examples of the disclosure may be described in the context of an aircraft manufacturing and service method 1000, as shown in FIG. 8, and an aircraft 1002, as shown in FIG. 9. During pre-production, example method 1000 may include specification and design 1004 of the aircraft 1002 and material procurement 1006. During production, component and subassembly manufacturing 1008 and system integration 1010 of the aircraft 1002 takes place. Thereafter, the aircraft 1002 may go through certification and delivery 1012 in order to be placed in service 1014. While in service by a customer, the aircraft 1002 is scheduled for routine maintenance and service 1016, which may also include modification, reconfiguration, refurbishment and the like.

Each of the processes of method 1000 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 9, the aircraft 1002 produced by example method 1000 may include an airframe 1018 with a plurality of systems 1020 and an interior 1022. Examples of high-level systems 1020 include one or more of a propulsion system 1024, an electrical system 1026, a hydraulic system 1028, and an environmental system 1030. Any number of other systems may be included. Although an aerospace example is shown, the principles of the invention may be applied to other industries, such as the automotive industry.

Apparatus and methods embodied herein may be employed during any one or more of the stages of the production and service method 1000. For example, components or subassemblies corresponding to production process 1008 may be fabricated or manufactured in a manner similar to components or subassemblies produced while the aircraft 1002 is in service. Also, one or more apparatus examples, method examples, or a combination thereof may be utilized during the production stages 1008 and 1010, for example, by substantially expediting assembly of or reducing the cost of an aircraft 1002. Similarly, one or more of apparatus examples, method examples, or a combination thereof may be utilized while the aircraft 1002 is in service, for example and without limitation, to maintenance and service 1016.

Although various embodiments of the disclosed system and method for dissipation of an electrostatic charge have been shown and described, modifications may occur to those skilled in the art upon reading the specification. The present application includes such modifications and is limited only by the scope of the claims.

What is claimed is:

1. A system for dissipation of an electrostatic charge comprising:
   an electrostatic discharge assembly configured to connect to a conductive article, said electrostatic discharge assembly comprising:
   a conductor comprising a conductive substrate comprising a first major surface and a second major surface, at least a portion of said first major surface of said conductive substrate defining a conductive surface;
   an insulator positioned between said conductor and said conductive article, said insulator comprising an insulative substrate comprising a first major surface connected to said second major surface of said conductive substrate and a second major surface connected to said conductive article;
   an indicator electrically connected to said conductor and said conductive article, said indicator comprising an indicator light, a first terminal comprising a first end electrically connected to said indicator light and a second end in electrical contact with said first major surface of said conductive substrate, and a second terminal comprising a first end electrically connected to said indicator light and a second end in electrical contact with said conductive article; and
   a protective substrate positioned overtop said conductive substrate, said insulative substrate, and said indicator, said protective substrate being connected to said conductive article and comprising a window configured to expose at least a portion of said conductive surface.

2. The system of claim 1 wherein said conductor and said insulator form a laminated assembly.

3. The system of claim 1 wherein said indicator light comprises a static electricity light bulb.

4. The system of claim 1 wherein said indicator light comprises a neon light bulb.

5. The system of claim 1 wherein said second end of said second terminal is disposed between said second major surface of said insulative substrate and a surface of said conductive article.

6. The system of claim 1 wherein said conductor comprises metal foil tape.

7. The system of claim 1 wherein said insulator comprises insulating tape.

8. The system of claim 1 wherein said window exposes at least 50 percent of said conductive surface.

9. The system of claim 1 wherein said window exposes at least 60 percent of said conductive surface.

10. The system of claim 1 wherein said window exposes at least 75 percent of said conductive surface.

11. The system of claim 6 wherein said metal foil tape comprises at least one of aluminum and copper.

12. The system of claim 1 wherein said insulator comprises foam.

13. A system for dissipation of an electrostatic charge comprising:
   a conductive article; and
   an electrostatic discharge assembly connected to said conductive article, said electrostatic discharge assembly comprising:
   a conductor comprising an electrically conductive material, said conductor further comprising a first major surface and a second major surface, at least a portion of said first major surface of said conductive substrate defining a conductive surface;

an insulator comprising an electrically insulative material, said insulator being positioned between said conductor and said conductive article, said insulator comprising a first major surface connected to said second major surface of said conductor and a second major surface connected to said conductive article;

an indicator electrically connected between said conductor and said conductive article, said indicator comprising an indicator light, a first terminal comprising a first end electrically connected to said indicator light and a second end in electrical contact with said conductor, and a second terminal comprising a first end electrically connected to said indicator light and a second end in electrical contact with said conductive article; and a protector positioned overtop said conductor, said protector being connected to said conductive article and comprising a window configured to expose at least a portion of said conductive surface, wherein an electrostatic charge brought into close approximation of said conductor will cause said electrostatic charge to be discharged through said indicator, said indicator being configured to visually indicate said discharge of said electrostatic charge.

14. The system of claim 13 wherein said conductor, said insulator, and said protector form a laminated assembly.

15. The system of claim 13 wherein said indicator comprises a static electricity light bulb.

16. The system of claim 13 wherein said indicator light comprises a neon light bulb.

17. The system of claim 13 wherein said conductive article comprises a handrail.

18. The system of claim 13 wherein said conductive article comprises a workbench.

19. A method for dissipation of an electrostatic charge, said method comprising:

providing a conductive article;

providing an electrostatic discharge assembly comprising a conductor, an insulator positioned between said conductor and said conductive article, an indicator electrically connected to said conductor and said conductive article, and a protector positioned overtop said conductor, said protector being connected to said conductive article and comprising a window configured to expose at least a portion of said conductor;

installing said electrostatic discharge assembly to said conductive article;

approximating a human body having a developed electrostatic charge to said electrostatic discharge assembly;

discharging said electrostatic charge;

confirming discharge of said electrostatic charge by visual observation of said indicator.

20. The method of claim 19 wherein said indicator comprises at least one of a static electricity light bulb and a neon light bulb.

* * * * *